US008652159B2

(12) United States Patent
Trissel et al.

(10) Patent No.: US 8,652,159 B2
(45) Date of Patent: Feb. 18, 2014

(54) LANCET

(75) Inventors: John Trissel, Canton, GA (US); Lauren R. Pusey, Woodstock, GA (US); Christopher J. Ruf, Marietta, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 314 days.

(21) Appl. No.: 12/829,076

(22) Filed: Jul. 1, 2010

(65) Prior Publication Data

US 2010/0280537 A1 Nov. 4, 2010

Related U.S. Application Data

(63) Continuation-in-part of application No. 29/339,576, filed on Jul. 2, 2009, now Pat. No. Des. 621,045, and a continuation-in-part of application No. 12/641,684, filed on Dec. 18, 2009, application No. 12/829,076, which is a continuation-in-part of application No. 12/510,701, filed on Jul. 28, 2009, now abandoned.

(60) Provisional application No. 61/222,567, filed on Jul. 2, 2009, provisional application No. 61/138,768, filed on Dec. 18, 2008, provisional application No. 61/084,456, filed on Jul. 29, 2008.

(51) Int. Cl.
*A61B 17/14* (2006.01)
*A61B 17/32* (2006.01)

(52) U.S. Cl.
USPC ........................................................ 606/181

(58) Field of Classification Search
USPC .......... 606/181–185, 172, 167; 600/583, 573, 600/576, 574, 584, 578; 604/117
See application file for complete search history.

(56) References Cited

U.S. PATENT DOCUMENTS

| 2,839,056 A | | 6/1958 | Mailly |
| 3,358,689 A | | 12/1967 | Higgins |
| 4,577,630 A | | 3/1986 | Nitzsche et al. |
| 4,580,564 A | * | 4/1986 | Andersen ...................... 606/172 |
| 4,889,117 A | | 12/1989 | Stevens |
| 5,314,442 A | * | 5/1994 | Morita .......................... 606/182 |

(Continued)

FOREIGN PATENT DOCUMENTS

| DE | 20114658 U1 | 11/2001 |
| EP | 1987770 A1 | 11/2008 |
| WO | WO2007097283 | 8/2007 |
| WO | 2009/006461 A1 | 1/2009 |

OTHER PUBLICATIONS

European Patent Office; International Search Report; Sep. 1, 2010; 15 pages.
European Office Action; Nov. 2, 2012; 4 pgs.

*Primary Examiner* — Thomas McEvoy
*Assistant Examiner* — Jocelin Tanner
(74) *Attorney, Agent, or Firm* — Gardner Groff Greenwald & Villanueva, PC

(57) ABSTRACT

A lancet for use with a lancing device, the lancet having a body with releasable engagement features for engagement with a cooperating portion of a lancing device, a sharp needle, and a removable endcap. A coupling portion of the lancet has a non-circular profile. The endcap includes a receptacle for covering the sharp lancet tip after use, and a sheath portion with relief openings to reduce bending of the needle during manufacture or during removal of the endcap.

18 Claims, 2 Drawing Sheets

(56) References Cited

U.S. PATENT DOCUMENTS

| | | | |
|---|---|---|---|
| 5,324,303 A | 6/1994 | Strong et al. | |
| 5,385,571 A * | 1/1995 | Morita | 606/181 |
| 5,454,828 A * | 10/1995 | Schraga | 606/181 |
| 5,569,286 A | 10/1996 | Peckham et al. | |
| 5,868,772 A | 2/1999 | LeVaughn et al. | |
| D445,183 S | 7/2001 | McWethy et al. | |
| 6,589,261 B1 | 7/2003 | Abulhaj et al. | |
| 6,602,268 B2 * | 8/2003 | Kuhr et al. | 606/181 |
| D484,244 S | 12/2003 | Starnes | |
| D493,527 S | 7/2004 | Szabo | |
| 6,890,319 B1 * | 5/2005 | Crocker | 604/131 |
| D533,943 S | 12/2006 | Chen | |
| D562,980 S | 2/2008 | Marshall | |
| D567,944 S | 4/2008 | Sarna | |
| 7,655,017 B2 | 2/2010 | Starnes | |
| 2003/0109895 A1 | 6/2003 | Taylor et al. | |
| 2004/0236251 A1 * | 11/2004 | Roe et al. | 600/583 |
| 2007/0162065 A1 * | 7/2007 | Li et al. | 606/182 |
| 2007/0288047 A1 | 12/2007 | Thoes et al. | |
| 2007/0293883 A1 * | 12/2007 | Horie | 606/181 |
| 2008/0027474 A1 | 1/2008 | Curry et al. | |
| 2008/0033468 A1 | 2/2008 | Lathrop et al. | |
| 2008/0082116 A1 | 4/2008 | Lathrop et al. | |
| 2010/0030249 A1 | 2/2010 | Pusey et al. | |

* cited by examiner

LANCET

CROSS-REFERENCE TO RELATED APPLICATIONS

This application claims priority benefit of U.S. Provisional Patent Application Ser. No. 61/222,567, filed Jul. 2, 2009; and is a continuation-in-part of U.S. Design patent application Ser. No. 29/339,576, filed Jul. 2, 2009; and is a continuation-in-part of U.S. patent application Ser. No. 12/641,684, filed Dec. 18, 2009, which claims priority to U.S. Provisional Patent Application Ser. No. 61/138,768, filed Dec. 18, 2008; and is a continuation-in-part of U.S. patent application Ser. No. 12/510,701, filed Jul. 28, 2009, which claims priority to U.S. Provisional Patent Application Ser. No. 61/084,456, filed Jul. 29, 2008; the entirety of which applications are all hereby incorporated herein by reference.

TECHNICAL FIELD

The present invention relates generally to the field of medical devices, and more particularly to lancets and lancing devices for blood sampling and testing.

BACKGROUND

Lancets and lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism, a charging mechanism for energizing the spring or other drive means of the drive mechanism, and a release mechanism for releasing the drive mechanism upon actuation. A lancet is typically propelled by the drive mechanism from a retracted position shielded within the housing to an extended position wherein a sharp tip portion of the lancet projects from the housing to prick the subject's skin at a desired lancing site. An ejection mechanism can optionally be included for discharge of a used lancet from the lancing device.

The lancet is typically a disposable component that is removably mounted into a receiver or lancet carrier portion of the drive mechanism of a lancing device. A used lancet typically is removed from the lancet carrier after sampling for disposal. A new, sterile lancet is then replaced into the lancet carrier for further sampling. Lancets typically comprise a sharp metal tip in the form of a needle or blade. The needle or blade is typically embedded in a plastic body that has a size and shape configured for releasable engagement with the receiver or lancet carrier of a lancing device. The sharp tip of the lancet is commonly embedded in a removable plastic cap to maintain sterility and prevent inadvertent sticks prior to use. The endcap may be replaceable onto the lancet after use to re-cover the sharp lancet tip for safety and hygienic purposes. It is to the provision of an improved lancet that the present invention is primarily directed.

SUMMARY

In example embodiments, the present invention relates to a proprietary lancet configured for insertion into a cooperating receiver of a lancing device. The lancet and lancing device include complementary engagement or coupling features for ensuring that only the proprietary lancet design is used with the lancing device. The engagement features provide a consistent lancet placement in the receiver, maintaining a consistent penetration depth and proper alignment for pain management.

The lancet optionally includes a fine gauge lancet needle, for example a 33-gauge needle. The lancet optionally also includes one or more relief channels in a removable endcap portion surrounding a sheath for retaining the lancet needle. The mold tooling that forms the relief channels directs the flow of plastic during injection molding of the lancet to reduce bending forces on the tip of the lancet needle during the molding process. The lancet optionally includes a non-circular periphery at its coupling area for engagement with the lancing device.

In one aspect, the present invention relates to a lancet including a lancet body having a rear end defining a coupling portion for connection to a lancing device, the coupling portion having a non-circular profile and at least one engagement feature for releasable engagement with a cooperating portion of the lancing device. The lancet also includes a needle having a sharp tip portion extending axially from the lancet body opposite the rear end, and an endcap removably secured to the lancet body and covering the sharp tip portion of the needle.

In another aspect, the invention relates to a lancet including a lancet body having a rear end defining a coupling portion for connection to a lancing device, the coupling portion having a non-circular profile with a width W and a thickness T defining an aspect ratio (W:T) of at least about 3:2. The lancet further includes a needle having a sharp tip portion extending axially from the lancet body opposite the rear end, and an endcap removably secured to the lancet body and covering the sharp tip portion of the needle.

In another aspect, the invention relates to a lancet including a lancet body, a needle having a sharp tip portion extending from the lancet body, and a removable endcap. The sharp tip portion of the needle is shielded within a sheath portion of the removable endcap, and at least one relief opening is provided within the removable endcap adjacent the sheath portion.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

DETAILED DESCRIPTION OF EXAMPLE EMBODIMENTS

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
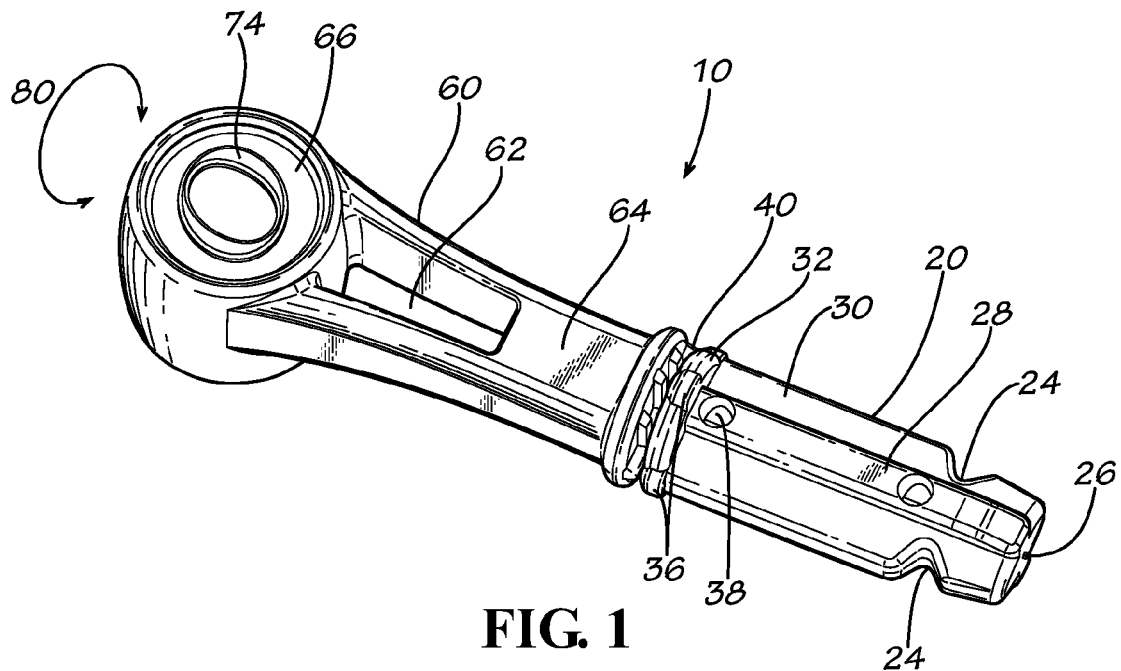
FIG. 1 is a first perspective view of a lancet according to an example embodiment of the present invention.
Figure 2:
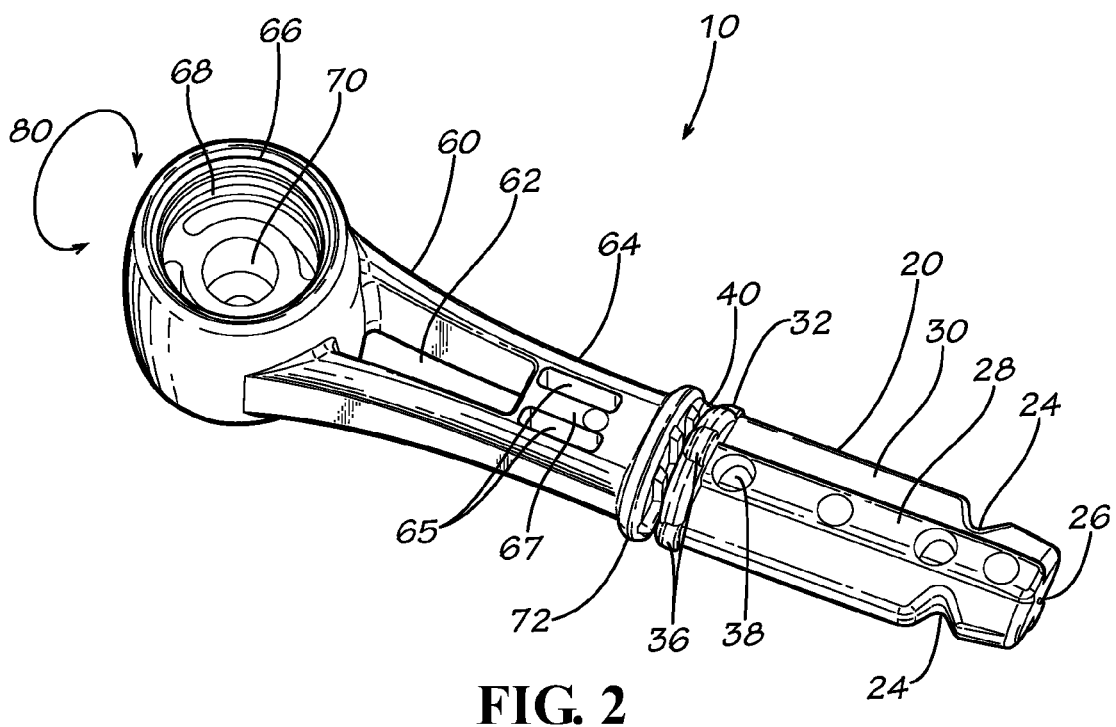
FIG. 2 is a second perspective view of the lancet of FIG. 1.
Figure 3:
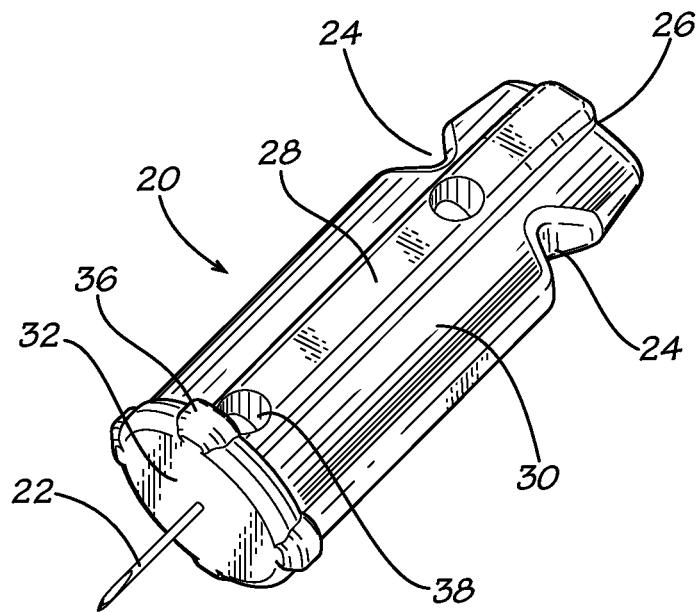
FIG. 3 is a perspective view of the lancet of FIG. 1, with an endcap portion thereof removed to expose the lancet needle.

With reference now to the drawing figures, wherein like reference numbers represent corresponding parts throughout the several views, FIGS. 1 and 2 show a proprietary interchangeable lancet 10, which includes lancet body 20, one or more breakaway connections or attachment webs 40, and an endcap 60. FIG. 3 shows the lancet 20 with the endcap 60 removed. In example embodiments, the lancet 10 has engagement features that are unique and complementary to a specified lancing device, so that only lancets of the proprietary design are usable with the lancing device, and preventing use of the lancing device with unauthorized lancets which may not be of adequate quality or safety, or which may lack the proper characteristics specified by the lancing device manufacturer or healthcare provider for a given application.

The lancet body 20 includes a needle 22, a rear end 26 for releasable engagement within a cooperating receiver or lancet holder portion of a corresponding lancing device design, a first pair of longitudinal protrusions or ribs 28 extending along at least a portion of its length on opposed top and bottom faces, a second pair of longitudinal protrusions or fins 30 extending along at least a portion of opposed side faces of the lancet body and arranged generally crosswise to the first pair of longitudinal protrusions or ribs 28, and a front end forming a transverse collar or flange 32. The lancet body 20 has a generally elliptical shaped periphery when viewed end-on or in cross-section, with the ribs 28 constituting the opposing ends of the short axis of the elliptical periphery and the fins 30 constituting the opposing ends of the long axis of the elliptical periphery. Other cross-sectional geometries are within the scope of the invention, including geometries having or being circumscribable within peripheral shapes including non-circular, rectangular, polygonal, square, triangular, circular and/or keyed. The ribs 28 and the fins 30 taper inwardly along their longitudinal axes towards the rear end 26. Along the sides of the fins 30 are formed an opposed pair of releasable engagement recesses 24 that are located proximally to the rear end. The front flange or collar 32 has a generally circular profile, with rounded protrusions 36 spaced crosswise along its perimeter. The lancet 20 optionally defines one or more recesses or holes 38, formed by mold tooling during manufacture for holding the lancet needle in position in the mold, and which reduce the amount of material required to manufacture the lancet.

The needle 22 includes a sharp tip portion extending axially from the lancet body 20 opposite the rear end 26. The needle can have a round cross-section, or can comprise a flat blade, or can be otherwise configured. Optionally, the needle 22 extends axially through the entire length of the lancet body, and a distal end of the needle is exposed at or extends beyond the rear end of the lancet body. Alternatively, the distal end of the needle is embedded within the lancet body. In example embodiments, the needle has a fine gauge, for example a 33-gauge needle, for lower mass and reduced pain during use.

The endcap 60 includes a body 64, a receiver cup or receptacle 66 for attachment over the lancet needle after use, and an end disk or flange 72. The body 64 tapers outwards along its longitudinal axis from the end disk 72 towards the receptacle 66. The end disk 72 contains a needle opening that receives the lancet needle 22 in the lancet's unused state. The endcap 60 may include branding indicia 74 or other information about the product on the receptacle 66 or elsewhere on the endcap and/or lancet body. The body may contain one or more material voids 62 to lessen the amount of material used to construct the needle cap. The end disk 72 has a generally circular cross section. The receptacle 66 contains an inner groove or snap coupling 68 and a central chamber or opening 70. The inner groove 68 releasably engages the round protrusions 36 of the lancet body to retain the lancet needle shielded within the cup 66 after use of the lancet to prevent accidental needle sticks. The central chamber or opening 70 receives the needle tip after use of the lancet to prevent breaking the tip and to provide easier attachment of the endcap onto the lancet body. In example embodiments of the invention, the depth of the chamber 70 is equal to or greater than the length of the exposed portion of the needle 22 extending from the lancet body.

The lancet 20 is connected to the lancet endcap 60 by one or more breakaway connections or webs 40. The breakaway connections or webs are thin bodies or protrusions that extend between the front disk 34 of the lancet body and the end disk 72 of the endcap that may be broken or separated by applying a torsional (indicated by direction arrow 80) and/or tension force to the needle cap 60 while holding the lancet body. The breakaway connections or webs 40 may be at least partially severed after molding to provide easier cap removal or may be molded in such a fashion that they are in close proximity to the opposing surface but not connect to it except in the center near the needle. The breakaway connections or webs 40 also serve to provide lateral support to resist bending between the lancet body and the endcap, which might otherwise result in bending of the lancet needle which could result in increased pain to the subject during lancing due to non-axial alignment of the needle tip.

The endcap 60 optionally includes a pair of relief openings, channels, or recesses 65 extending along a portion of the endcap body 64 proximal the end disk or flange 72. During the molding process, tool inserts of the mold that form these recesses 65 channel the flow of plastic to form a sheath 67 extending between the recesses that surrounds the tip of the lancet needle 22. Controllably directing the flow of plastic during molding in this manner reduces or eliminates the application of non-axial bending forces on the lancet needle during manufacture, providing a more straight and axially aligned needle tip and thereby reducing pain during use of the lancet. The relief openings 65 may also permit flexure of the sheath 67 during removal of the endcap to further reduce the imposition of bending forces on the needle tip. In example embodiments, the sheath is formed of a sufficiently deformable resilient material and the thickness of the sheath and the dimensions of the relief openings are selected to result in a sheath stiffness that is less than the stiffness of the lancet needle, such that the sheath bends before the needle. For example, the relief openings may have a length of at least about one-third to one-half the length of the exposed portion of the needle, and/or the width of the relief openings is at least about 0.5 to 1.0 times the thickness of the sheath.

The endcap 60 is optionally at least as long as the lancet body 20, to provide easier manipulation and use of the lancet. In example embodiments, the receiver cup 66 of the endcap has a transverse dimension or diameter that is substantially greater than the width or thickness of the body portion 64 of the endcap, optionally comprising a smoothly tapered or flared transition portion extending therebetween, for gripping during use of the lancet. In the depicted embodiment, the ribs 28 and fins 30 extend along substantially the entire length of the lancet body. In alternate embodiments, the ribs 28 and/or the fins 30 comprise one or more protrusions or bosses extending along a portion of the length of the lancet body, for example positioned at spaced apart locations on the lancet body.

Figure 4:
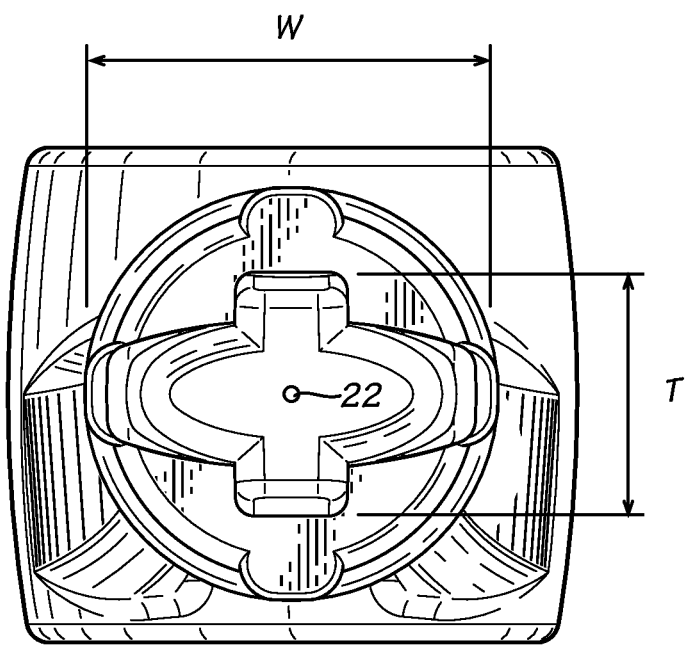
FIG. 4 is a rear end view of the lancet of FIG. 1.

In example forms, and as seen with reference to FIG. 4, the rear end 26 of the lancet body 20 presents a non-circular periphery having a width-to-thickness aspect ratio of about 3:2, or of greater than 3 to 2. In other words, the side-to-side width W of the opposed fins 30 is about one and one-half times the top-to-bottom thickness T of the opposed ribs 28. In example forms, the lancet body (the overall lancet 10 with the endcap 60 removed) has a mass of about 0.15 g or less, and more preferably a mass of no more than 0.13 g, thereby providing a low-mass lancet which may reduce the sensation of pain during use. In example forms, the overall length of the lancet body and needle, from the rear end 26 of the body to the tip of the needle 22, is about 16.5 mm, and the length of the lancet body without the needle is about 13 mm.

In use, the lancet 10 is installed into a lancet carrier of a lancing device, rear end 26 of the lancet body 20 first, until the engagement recesses 24 are engaged with cooperating cantilevers or other releasable engagement structures of the lancing device. Engagement of the lancet into the lancing device optionally provides tactile and/or audible feedback to the user to indicate that the engagement structures of the lancing device are fully engaged inside the lancet's engagement recesses. The user then detaches the endcap 60 from the lancet body 20 by separating the breakaway connection webs 40. The non-circular profile of the portion of the lancet body engaged with the lancet carrier prevents the lancet 20 from rotating as the endcap 60 is twisted for removal. The endcap 60 is then axially removed from the lancet needle 22 to expose the sharp tip. The lancing device is charged or cocked, and is then ready for actuation to pierce the subject's skin at the lancing site to generate a sample. The ribs 28 and fins 30 assist in maintaining alignment of the lancet during the lancing stroke, to ensure axial alignment of the lancing needle as it pierces the skin in order to minimize pain. Once the lancet 20 has been used, the lancet needle 22 can be re-covered by placement of the endcap receptacle 66 over the sharp tip of the lancet needle and engaging the protrusions 26 of the lancet body onto to the inner groove 68 of the endcap. The body 64 of the endcap may be used as a handle for the lancet needle cap, and may allow easier re-covering of the lancet needle 22.

While the invention has been described with reference to preferred and example embodiments, it will be understood by those skilled in the art that a variety of modifications, additions and deletions are within the scope of the invention, as defined by the following claims.

What is claimed is:

1. A lancet comprising:
   a lancet body having a rear end defining a coupling portion for connection to a lancing device, the coupling portion comprising a pair of opposing longitudinal ribs and a pair of opposing longitudinal fins arranged in a generally cross-wise manner wherein at least one of the pair of longitudinal ribs and the pair of longitudinal fins taper inwardly along their defined longitudinal axes toward the rear end of the lancet body, whereby the coupling portion comprises a non-circular profile and at least one engagement feature for releasable engagement with a cooperating portion of the lancing device, and wherein the non-circular profile of the coupling portion of the lancet body has a width W and a thickness T defining an aspect ratio (W:T) of about 3:2 or greater;
   a needle having a sharp tip portion extending axially from the lancet body opposite the rear end; and
   an endcap removably secured to the lancet body and covering the sharp tip portion of the needle.

2. The lancet of claim 1, wherein the at least one engagement feature of the lancet body comprises at least one recess in the lancet body.

3. The lancet of claim 2, wherein the at least one engagement feature of the lancet body comprises an opposed pair of recesses in transverse sides of the lancet body.

4. The lancet of claim 1, wherein the endcap comprises a receptacle for enclosing the sharp tip portion of the needle after the lancet is used.

5. The lancet of claim 4, wherein the endcap has a proximal end and a distal end, the proximal end of the endcap being initially secured to the lancet body and covering the sharp tip portion of the needle, and the distal end of the endcap comprising the receptacle for enclosing the sharp tip portion of the needle after the lancet is used.

6. The lancet of claim 5, wherein the endcap has relief cutouts alongside a sheath adjacent its proximal end, the sheath initially surrounding the sharp tip portion of the needle.

7. The lancet of claim 1, wherein the lancet body and the needle have a combined mass of no more than 0.15 g.

8. The lancet of claim 1, wherein the lancet body and needle have a combined length of about 16.5 mm.

9. The lancet of claim 1, wherein the lancet body has a length of about 13 mm.

10. The lancet of claim 1, in combination with a lancing device comprising the cooperating portion for releasable engagement with the lancet, the engagement feature of the lancet and the cooperating portion of the lancing device being complementary and unique to prevent use of the lancing device with other lancet types.

11. A lancet comprising:
    a lancet body having a rear end defining a coupling portion for connection to a lancing device, the coupling portion comprising a pair of opposing longitudinal ribs and a pair of opposing longitudinal fins arranged in a generally cross-wise manner wherein the longitudinal ribs and fins taper inwardly along their defined longitudinal axes toward the rear end of the lancet body, whereby the coupling portion comprises a non-circular profile with a width W and a thickness T defining an aspect ratio (W:T) of at least about 3:2;
    a needle having a sharp tip portion extending axially from the lancet body opposite the rear end; and
    an endcap removably secured to the lancet body and covering the sharp tip portion of the needle.

12. The lancet of claim 11, wherein the coupling portion comprises an opposed pair of recesses directed inwardly into the lancet body.

13. The lancet of claim 12, wherein the inwardly directed recesses are generally V-shaped, having angularly inclined forward and rear contact faces.

14. The lancet of claim 11, wherein the endcap further comprises a receptacle having a depth sufficient to receive the sharp tip portion of the needle.

15. The lancet of claim 11, wherein the endcap has relief cutouts alongside a sheath portion into which the sharp tip portion of the needle is embedded.

16. The lancet of claim 11, wherein the lancet body and the needle have a combined mass of no more than 0.15 g.

17. The lancet of claim 11, wherein the lancet body and the needle have a combined length of about 16.5 mm.

18. The lancet of claim 11, wherein the lancet body has a length of about 13 mm.

* * * * *